United States Patent [19]

Satchell

[11] Patent Number: 4,569,764

[45] Date of Patent: Feb. 11, 1986

[54] COLLECTION DEVICE WITH PHASE PARTITIONING MEANS

[75] Inventor: Fred E. Satchell, Chesterfield, Mo.

[73] Assignee: Sherwood Medical Company, St. Louis, Mo.

[21] Appl. No.: 260,459

[22] Filed: May 4, 1981

Related U.S. Application Data

[63] Continuation of Ser. No. 31,817, Apr. 20, 1979, abandoned.

[51] Int. Cl.[4] .............................................. B01D 21/26
[52] U.S. Cl. .................................... 210/511; 210/516; 210/927
[58] Field of Search ............... 210/511, 514, 515, 516, 210/DIG. 24, 927; 422/101, 102; 222/94, 136, 386.5; 128/764, 765, DIG. 28, 766, 272, 272.1, 272.3; 206/219, 220, 221, 222; 23/230 B; 215/DIG. 8; 233/1 A, 1 R, 26

[56] References Cited

U.S. PATENT DOCUMENTS

| | | | |
|---|---|---|---|
| 2,815,152 | 12/1957 | Mills | 222/386.5 |
| 3,567,028 | 3/1971 | Nose | 210/232 |
| 3,655,035 | 4/1972 | Muhlbauer | 206/47 A |
| 3,852,194 | 12/1974 | Zine, Jr. | 210/927 X |
| 3,920,549 | 11/1975 | Gigliello et al. | 210/516 X |
| 3,957,654 | 5/1976 | Ayres | 210/516 |
| 3,976,579 | 8/1976 | Bennett | 210/516 |
| 3,981,804 | 9/1976 | Gigliello | 210/516 |
| 3,997,442 | 12/1976 | Gigliello et al. | 210/927 X |
| 4,021,340 | 5/1977 | Zine, Jr. | 210/515 X |
| 4,046,699 | 9/1977 | Zine, Jr. | 210/516 |
| 4,055,501 | 10/1977 | Cornell | 210/516 |
| 4,083,788 | 4/1978 | Ferrara | 210/516 |
| 4,088,582 | 5/1978 | Murty et al. | 210/516 |
| 4,246,123 | 1/1981 | Cornell et al. | 210/515 X |

Primary Examiner—David Sadowski
Attorney, Agent, or Firm—Stanley N. Garber; Andrew J. Beck; William R. O'Meara

[57] ABSTRACT

A fluid collection device is provided which includes a container for receiving a liquid, such as blood, which is centrifugally separable into relatively light and heavy phases, and a phase partitioning device in the container. The partitioning device includes a bag filled with a thixotropic gel-like sealant having a specific gravity between the specific gravities of the separated light and heavy phases. During centrifugation, the components of the cellular phase cause collapse of the bag and the flow of sealant through an outlet in the bag. The sealant flows to the interface between the two phases during centrifugation and provides a barrier between the separated phases.

21 Claims, 7 Drawing Figures

COLLECTION DEVICE WITH PHASE PARTITIONING MEANS

This application is a continuation of application Ser. No. 031,817, filed Apr. 20, 1979, now abandoned.

BACKGROUND OF THE INVENTION

This invention relates to fluid collection devices, and more particularly, to blood collection devices having means for partitioning the relatively light phase from the relatively heavy phase.

When taking blood samples for test purposes, whole blood is generally drawn into an evacuated collection tube and tube subsequently centrifuged to separate the blood into its relatively light phase, serum or plasma, and its heavier cellular phase. Blood phase separators or partitioning devices have been used to provide a partition or barrier between the separated phases until the light phase is removed for clinical testing. Many types of blood phase partitioning devices have been proposed, all with varying degrees of success. Some proposed partitioning arrangements included the use of a sealant of gel-like thixotropic material having a specific gravity intermediate the specific gravities of the light and heavy blood phases so that during centrifugation and phase separation, the sealant flows to the interface of the two phases and forms a partition between them. Various gel-like thixotropic materials or sealants are now well known. For example, in U.S. Pat. No. 3,852,194, a mixture of silicone and hydrophobic silicon dioxide powders is used to form a partition between the separated phases. In U.S. Pat. Nos. 4,021,340; 4,088,582 and 4,055,501, mixtures including liquid polybutene polymer and silicon dioxide powders are used as phase partitioning materials.

A serious problem in utilizing such partitioning materials is that the partition is sometimes formed too soon after centrifugation begins so that some blood cells are trapped above the partition in contact with the serum or plasma after phase separation. Such cells tend to contaminate the lighter phase and in some cases to such a degree that certain test results are unreliable or inaccurate. Cells have been trapped in or above the partition because the rising partitioning material engages descending cells and carries them to the interface of the two phases.

Also, in some cases, the separated serum was found to have excessive lactic dehydrogenase (LDH) which was believed to be caused by hemolysis of red cells due to the impact of the cells with the partitioning material under the influence of centrifugal forces. Where this occurs, the test results are inaccurate since some of the LDH indicated is caused by the process, that is, due to centrifugal separation and partitioning of the phases.

SUMMARY OF THE INVENTION

Accordingly, it is an object of the present invention to provide a fluid collection device having partitioning means forming a partition between separated light and heavy phases of a multi-phase liquid, such as whole blood, during centrifugation while minimizing components of the heavy phase remaining in the light phase, and in the case of blood, minimizing hemolysis of blood cells during centrifugation.

In accordance with one form of the present invention, a fluid collection device for receiving a liquid separable into relatively light and heavy phases is provided with a phase partitioning device that includes a collapsible container and a sealant material in the container. The sealant material has a specific gravity intermediate the specific gravities of the separated light and heavy phases and is flowable out of the container during phase separation and centrifugation of the device to form a partition between the separated phases.

These, as well as other objects and advantages of the present invention, will become apparent from the following detailed description and drawings.

DESCRIPTION OF THE PREFERRED EMBODIMENTS

Figure 1:
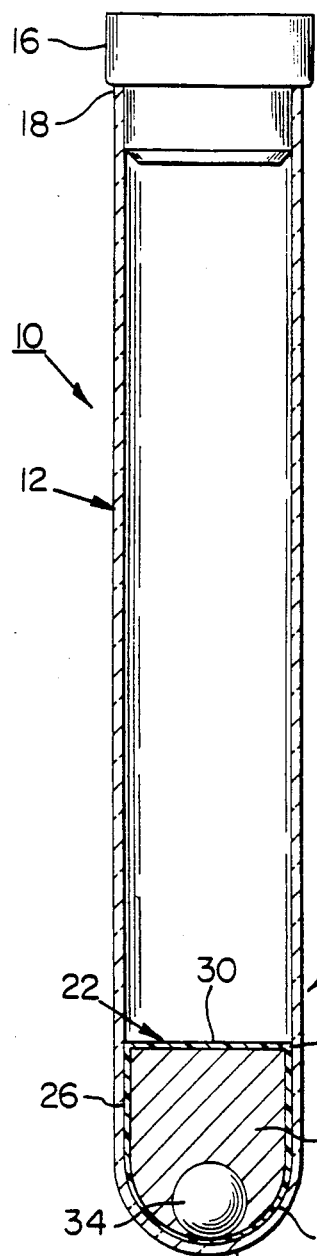
FIG. 1 is an elevational cross-sectional view of a blood collection device in accordance with a preferred embodiment of the present invention.
Figure 2:
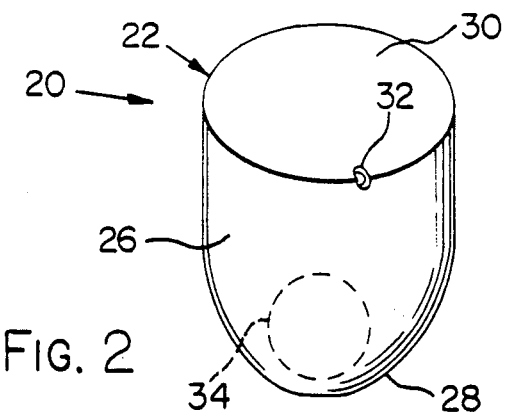
FIG. 2 is a perspective view, on an enlarged scale of the phase partitioning device used in the collection device of FIG. 1.

Referring now to the drawings, and particularly to FIGS. 1 and 2, a blood collection device 10 is shown including a blood collection container or tube 12 having a lower end 14 formed integrally with the tube, a stopper 16 closing the upper end 18 of the tube, and a blood phase partitioning device 20 disposed within tube 12. Stopper 16 is made of a suitable rubber which is pierceable by a needle cannula for introducing a sample of blood into the tube, and is self-sealing when the needle cannula is removed. Tube 12 is preferably made of glass and is air-evacuated to provide a negative pressure within the tube for facilitating the flow of blood into the tube.

The phase partitioning device 20 includes a collapsible container, such as a flexible bag 22, and a gel-like sealant material 24, which will be discussed hereinafter, that fills the bag 22.

Bag 22, which is shown disposed in the bottom of tube 12, has a generally cylindrical sidewall 26, an integral rounded or convex bottom wall 28 which generally conforms to the inner bottom wall of tube 12, and an upper flat wall 30 integral with the other walls. At the junction of the upper wall 30 with sidewall 26 there is provided a relatively small opening or sealant outlet 32. Bag 22 is made of a suitable pliable material such as a plastic, for example, polyethylene, polyvinyl chloride, or the like, and may be formed by conventional blow molding methods. The bag 22 is preferably formed of a material having a specific gravity greater than that of the cellular phase. The sealant filled bag may be inserted and cemented to the bottom of tube 12 by using a suitable adhesive or, as illustrated in FIG. 1 of the drawings, a weight 34, shown as a ball, for example, a metal ball bearing, may be provided within the bag during manufacture.

The sealant 24 is a thixotropic gel-like material that is substantially water insoluable and inert to the components of blood, and has a specific gravity intermediate the specific gravities of the separated light phase, serum or plasma, which is about 1.03, and the heavy cellular phase which is about 1.09. Preferably, the sealant is formed to have a specific gravity between about 1.035 and 1.06. The sealant 24 at rest and under normal handling and shipping conditions is semi-solid or non-flowable, but when subjected to forces such as centrifugal forces occurring during separation of the blood phases, becomes flowable. Upon cessation of such centrifugal forces the sealant returns to its semi-solid or non-flowable state.

As previously mentioned herein, the sealant material may be, for example, a mixture of silicone and hydrophobic silicon dioxide powders or a mixture of liquid polybutene polymer and silicon dioxide powder. One specific example of a useful sealant is described in U.S. Pat. No. 4,088,582, and includes 100 parts by weight of liquid polybutene (Polybutene Grade 24—Chevron Chemical Company of San Francisco, Calif.), 20 parts by weight of hydrophillic silica powder (Min-U-Sil 10, PGS, a subsidiary of ITT, Pittsburgh, Pa.), and 9 parts by weight of a hydrophobic silica powder (Aerosil R-972, Degussa Inc., Pigments Division, New York, N.Y.). The latter silica powder was made hydrophobic by a process including flame hydrolysis of silicate, and then reacting the silica with dimethyl dichlorosilane and steam. By varying the proportions of polybutene and silica powders desired viscosity and specific gravity characteristics can be obtained.

A sample of blood may be drawn into the blood collection device 10 by using a double-ended needle cannula such as provided by a conventional needle holder and tube guide. For example, after the distal end of the cannula is inserted into the vein of a patient, the device 10 is moved onto the proximal end of the cannula until the cannula pierces stopper 16, whereupon whole blood flows into tube 12. The filled tube is subsequently placed in a centrifuge such that the lower end 14 will be radially outwardly of the stopper and axis of rotation of the centrifuge during centrifugation. As is well known, if it is desired to separate serum, a blood clot is formed before centrifuging the device.

Figure 3:
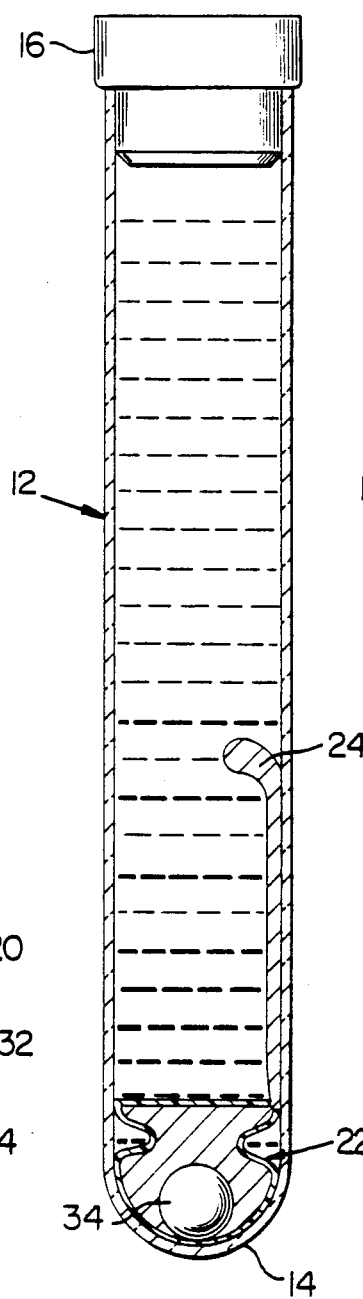
FIG. 3 is an elevational cross-sectional view of the collection device of FIG. 1 after blood has been drawn into it and while it is being centrifuged to separate the relatively light and heavy phases of blood.

During centrifugation, blood cells and other components of the heavy or higher density cellular phase move downwardly toward the lower end 14 of tube 12, while the light or lower density phase components move toward the upper end 18. Components of the heavy cellular phase are centrifugally urged radially outwardly or downwardly as viewed in the drawing against the upper wall 30 of bag 22, producing the pressure necessary to cause the bag to collapse and the sealant material 24 to flow out of the opening 32 and toward the upper end 18 of the tube, as illustrated in FIG. 3. Since the sealant 24 has a specific gravity between the specific gravities of the separated lighter and heavier phases, it seeks the interface of the separated phases and forms a partition or barrier across the tube at the interface between the two separated phases.

Figure 4:
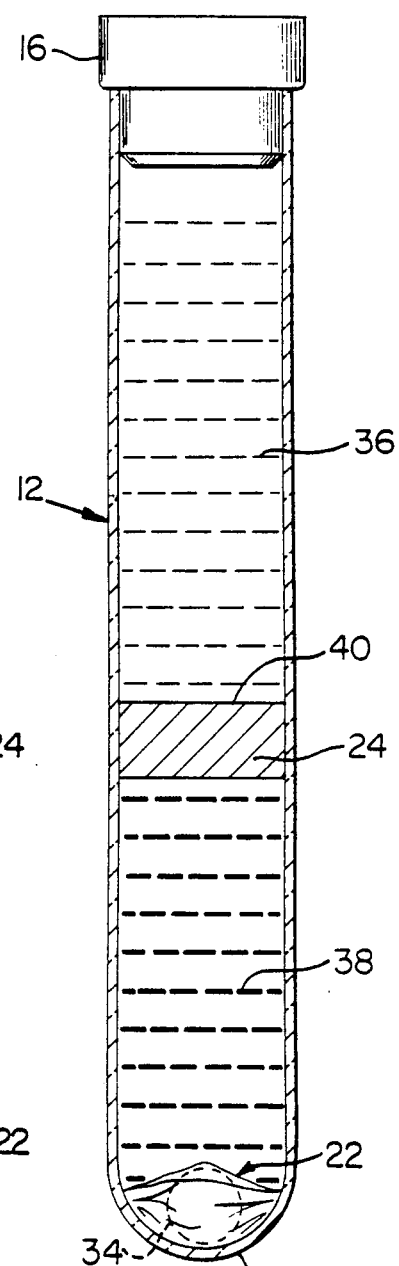
FIG. 4 is an elevational cross-sectional view of the collection device of FIG. 1 after complete blood separation and centrifugation.

In FIG. 4, where the device is illustrated in its condition after centrifugation and complete phase separation, the separated light and heavy phases are indicated at 36 and 38, respectively, and the partition between the phases is indicated at 40. Partition 40 is a liquid impervious seal or barrier disposed between the upper surface of the heavy phase 38 and the lower surface of the light phase 36. Since the partition 40 is formed of the thixotropic gel-like material 24, it provides a semi-rigid or non-flowable seal, so that after centrifugation, the collection device can be subjected to normal handling while the partition remains as a barrier between the two phases.

Since the outlet 32 is adjacent the sidewall of tube 12, the sealant 24 tends to stay close to the inner sidewall of the tube as it rises toward the upper end 18, as is apparent in FIG. 3, so that the sealant presents minimal interference to the movement of cellular components downwardly toward tube end 14. Because substantially less blood cells engage the rising sealant, there is less blood cell hemolysis due to such engagement and there is less chance of cells being carried upwardly to contaminate the light phase. Also, the size of the outlet 32 can be varied to meter sealant flow from the bag to provide a desired delay time, that is, to restrict the flow of sealant from bag 22 such that the seal 40 (FIG. 4) is not formed until substantially all of the cells have been separated from the light phase 36. Preferably, the flow of sealant is restricted so that it does not form a transverse seal across the interior of the tube until all or most of the cells have moved below that point along the tube where a seal is first formed. The bag 30 also provides a convenient container for handling the sealant and inserting it into the collection tubes during manufacture of device 10.

Figures 5, 6, 7:
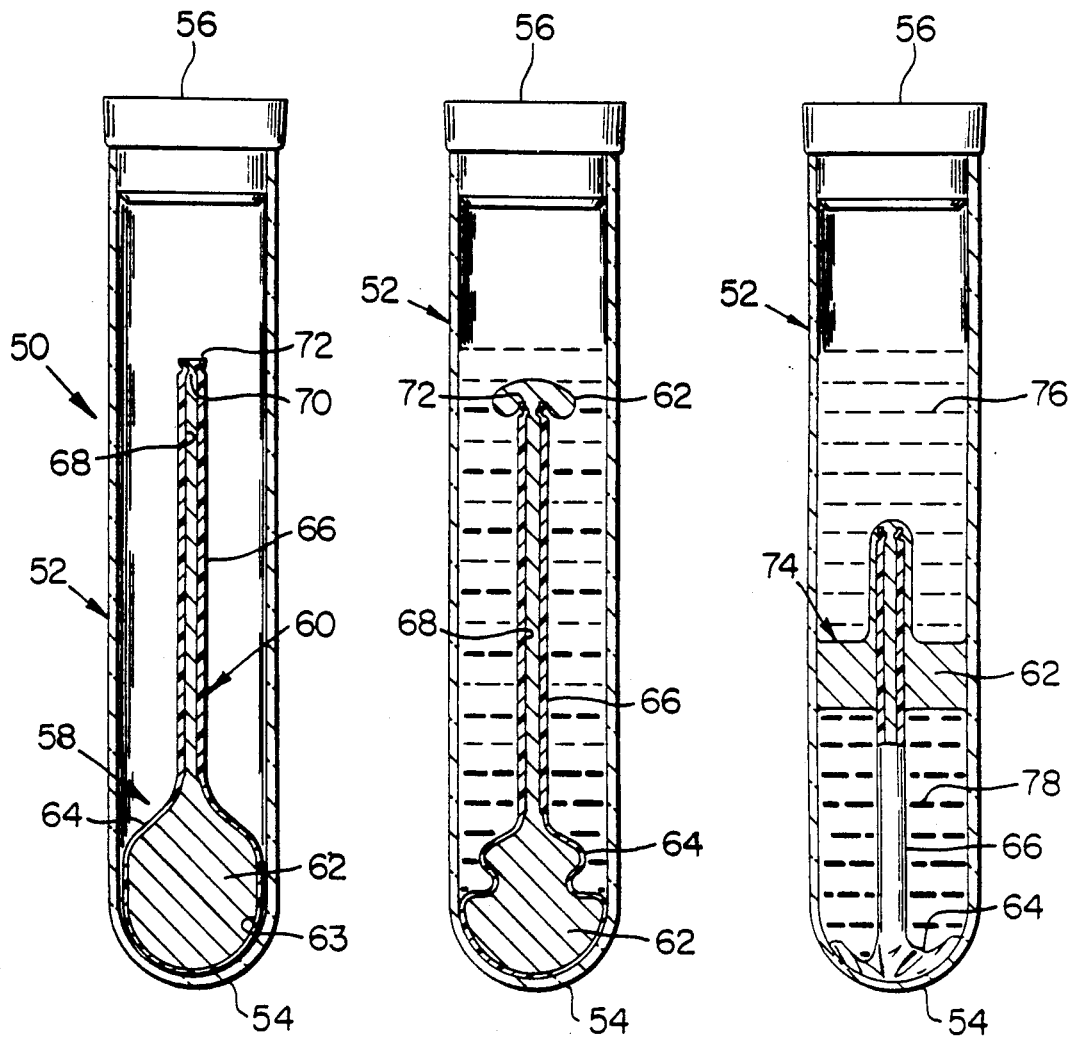
FIG. 5 is an elevational cross-sectional view of a blood collection device in accordance with a modified preferred embodiment.
FIG. 6 is an elevational cross-sectional view of the collection device of FIG. 5 after blood has been drawn into it and while it is being centrifuged to separate the blood phases.
FIG. 7 is an elevational cross-sectional view of the blood collection device of FIG. 5 after complete blood separation and centrifugation.

In FIGS. 5-7, a collection device 50 of modified construction is shown including a glass collection tube 52 having a lower, closed, integral end 54, and a stopper 56 closing the upper open end of the tube. Disposed within tube 52 is a phase partitioning device 58 which includes a collapsible container 60 made of a pliable plastic, and which may be formed by blow molding polyethylene or the like. Container 60 is filled with a thixotropic gel-like material or sealant 62 which may be identical to the sealant 24 of FIG. 1. Container 60 is preferably connected at the bottom to the lower inner wall of tube 12 such as by a suitable cement (not shown).

The container 60 has a lower collapsible balloon or bag 64 conforming to the lower portion of tube 52 which provides a reservoir 63 for the sealant 62. The reservoir 63 tapers at the top and connects with an integral, upwardly axially extending tube or standpipe 66 which is also filled with the sealant 62. Preferably, the sidewalls of standpipe 66 are made thicker, as shown, or of more rigid material, than the sidewalls of the bag portion 64 so that the pipe is more rigid and will stand vertically when the phase partitioning device 58 is disposed in the tube as shown. The pipe 66 provides a sealant flow passage 68 which is shown with a narrowed portion or restriction 70 near the upper end of the pipe. The passage 68 is open at the bottom and communicates with the reservoir 63, and has an upper open end or outlet 72. The container 60 is completely closed except at the outlet 72.

While standpipe 66 is shown coaxial with tube 52, the standpipe may be formed so that its longitudinal axis is offset or radially displaced from the longitudinal axis of the tube. In copending application Ser. No. 031,818 filed on Apr. 20, 1979, now U.S. Pat. No. 4,246,123 the same filing date as this application, having the same assignee as this application, and entitled "Fluid Collection Device With Phase Partitioning Means", a standpipe is disclosed which is displaced from the longitudinal axis of the collection container. By offsetting the standpipe in this manner, a blood clot, in the case of serum separation, can more readily pass by the standpipe, that is with little or no interference from the standpipe.

Tube 52 is preferably air evacuated to provide a negative pressure within the tube so that a double-ended needle may be used as described in connection with the embodiments shown in FIGS. 1-4 to collect a blood sample from a patient. After blood has been drawn into the tube and a blood clot formed (where serum is desired), the tube is placed in a centrifuge to separate the phases. FIG. 6 illustrates the tube 52 when filled with blood and during phase separation and centrifugation. As the heavier phase components, including the blood cells, move toward the bottom under centrifugal forces, the bag or reservoir portion 64 tends to collapse, causing sealant 62 to move upwardly in passage 68 of pipe 66 and out the outlet 72. Because of the relatively small cross-sectional area of passage 68 and the restriction 70, there is a time delay which allows most or substantially all of the cells to move below the outlet 72 of pipe 66 before the sealant 62 issues from the pipe 66 in a significant amount. As the centrifugation continues, the heavier phase moves downwardly in the tube 52 toward closed end 54, further collapsing bag 64 and moving more sealant 62 upwardly in the pipe and the light phase rises upwardly in the tube. After complete phase separation and centrifugation, FIG. 7 shows the sealant 62 forming a partition 74 entirely across the tube interior which provides a liquid impervious barrier or seal between the separated upper phase or serum, indicated at 76, and the lower cellular phase, indicated at 78. As seen in FIG. 7, the bag 64 is substantially completely collapsed with some sealant 62 closing the upper portion of the passage 68. In this embodiment, sealant 62 does not engage or come in contact with the cellular blood components while it is rising from the bottom of the tube through the cellular phase to the interface.

While the hematocrit ratio, and therefore the upper level of the separated cellular phase will vary for different patients, the pipe 66 is desirably made so that its outlet 72 will be above the normally expected upper level of the separated cellular phase for the typical patient when the bag portion 64 is collapsed. Preferably, the outlet is above the major portion of the sealant of the partition 74 or near the upper level of the partition. One desirable construction using a 16×127 mm glass tube, an 85% draw (12.2 ml), 1 cm (1.5 ml) minimum barrier height, and effective for hematocrits up to about a 50%, may employ a bag having a standpipe with a total initial height of about 3 mm. The inner diameter of the standpipe may be, for example, about 0.15 inch.

Where it is desired to separate plasma instead of serum, the whole blood may be placed in the centrifuge immediately after taking it and an anticoagulant may be used where desired. In such case, no clot is formed but the cells all go to the lower portion and are separated by the sealant material from the upper lighter phase or plasma.

In each of the above-described embodiments, the restriction or outlet 32 or 72 is preferably sized to provide a time delay allowing cells to move downwardly such that they are below the first layer that is formed across the interior of the tube. Also, since the sealant moves closely along the inner sidewall in the embodiment shown in FIGS. 1-4, and within the passage 68 in the embodiment shown in FIGS. 5-7, there is less likelihood of the sealant trapping cells and causing them to remain on top of the sealant, and this reduces the chance of significant cell contamination of the lighter phase. Furthermore, because of the flow along the inner wall of the collection tube or within the passage 68, fewer cells collide with the sealant resulting in less hemolysis of blood cells due to sealant and cell collision and, therefore, less LDH caused by the phase separation process. The pipe 66 of the embodiment of FIGS. 5-7 also causes the partition 74 to be formed from the bottom upwardly so that the upper surface of the partition is less likely to trap or contain cellular material which could contaminate the serum or plasma.

As various changes could be made in the above construction without departing from the scope of the invention, it is intended that all matter contained in the above description or shown in the accompanying drawings shall be interpreted as illustrative and not in a limiting sense.

What is claimed is:

1. A fluid collection device for receiving a liquid separable into relatively light and heavy phases during centrifugation of the device comprising a collection container for receiving the liquid and having an open upper end and a closed lower end, stopper means closing said upper end, and phase partitioning means in said collection container, said phase partitioning means comprising a unitary collapsible container adjacent said lower end and having an opening therein, and a gel-like thoxitropic sealant material in said collapsible container having a specific gravity intermediate the specific gravities of the separated light and heavy phases, said collapsible container having wall portions thereof of pliable material which are deformable under centrifugal forces during centrifugation to cause said sealant material to flow through said opening to a location between the lighter and heavier phases to form a partition separating the light and heavy phases and spaced from and independent of said collapsible container, said phase partitioning means including means for maintaining said collapsible container adjacent said lower end of said collection container during phase separation and centrifugation.

2. The device of claim 1 wherein said opening is adjacent the sidewall of said collection container.

3. The device of claim 1 wherein said maintaining means includes a weight having a specific gravity greater than that of the heavy phase.

4. The device of claim 1 wherein said maintaining means includes an adhesive.

5. The device of claim 1 wherein said collapsible container is a pliable plastic bag.

6. The device of claim 1 wherein said phase partitioning means includes a standpipe connected with said collapsible container opening and extending upwardly in said collection container and having an outlet adjacent the upper end thereof located such that said sealant flows up said standpipe and out said outlet at a point above the upper surface of the separated heavier phase.

7. The device of claim 1 wherein said collapsible container is a collapsible pliable bag, and said sealant material is flowable to said location to form said partition which partition is separated from said bag by the heavy phase after phase separation.

8. A blood collection device for receiving a sample of whole blood adapted to be separated into its relatively light phase, serum or plasma, and its heavy cellular phase during centrifugation of the device comprising a collection container for receiving the sample of blood and having closed upper and lower ends, said upper end being closed by stopper means, and phase partitioning means in said container including a unitary collapsible pliable bag adjacent said lower end and having an opening therein, said bag having pliable wall portions thereof deformable under centrifugal forces during blood phase separation to effect collapse of said bag, and a gel-like thixotropic sealant material in said bag having a specific gravity intermediate the specific gravities of the separated light and heavy phases, said bag being collapsible to cause said sealant to flow through said opening in response to centrifugal forces urging the components of the heavy phase toward said bag and lower end during phase separation and centrifugation of the device, said sealant being flowable from said bag during centrifugation to a location between the light and heavy phases and spaced from said bag to form a liquid impervious barrier between the two phases independently of said bag.

9. The device of claim 8 wherein said sealant comprises a gel-like material having a specific gravity between about 1.03 and 1.06.

10. The device of claim 8 wherein said opening is adjacent the sidewall of said container.

11. The device of claim 8 or 10 further including a needle-pierceable stopper closing the upper end of said container, said container being evacuated for facilitating the reception of blood when said stopper is pierced by a needle for transferring blood into said container.

12. The device of claim 11 including means for maintaining said bag adjacent said lower end of said container during phase separation and centrifugation.

13. The device of claim 8 further including an integral standpipe connected to said opening and having an outlet adjacent the upper end thereof located such that said sealant issues from said standpipe during centrifugation at a location which is above the upper level of the heavy phase when completely separated.

14. The device of claim 13 wherein said standpipe has a reduced portion to provide a restriction for the flow of sealant from said pipe to delay the formation of said barrier until substantially all of the blood cells have moved below said outlet.

15. The device of claim 14 further including means for securing said bag to said lower end of said container.

16. The device of claim 8 or 13 wherein said bag is formed of a relatively thin, pliable, plastic material.

17. The device of claim 16 wherein said bag is of a polyvinyl chloride.

18. The device of claim 8 wherein said opening restricts the flow of said sealant therefrom to delay the formation of said barrier across the container until substantially all of the cells are below the level of the barrier, to prevent trapping cells above the barrier.

19. The device of claim 1, 8 or 7 wherein said lower end of said collection container is closed by an integral portion of said collection container.

20. A blood collection device for receiving a whole blood sample and for centrifugally separating it into its relatively light and heavy blood phases and for providing a partition between the separated phases during centrifugation of the device comprising a blood collecting container, a unitary collapsible pliable bag in said container and which has pliable wall portions that are of a material which is deformable under centrifugal forces during and after phase separation and centrifugation to effect collapse of said bag, said bag having an opening therein, and a gel-like thixotropic sealant in said bag having a specific gravity intermediate the specific gravities of the separated phases and flowable through said opening and away from said bag to a location between the separated blood phases in response to the collapse of said bag during centrifugation of the device to form a partition between the separated phases which is spaced from and independent of said bag.

21. The device of claim 1, 8 or 20 wherein said wall portions are non-self-supporting pliable wall portions.

* * * * *